(12) United States Patent
Wade et al.

(10) Patent No.: US 12,290,412 B2
(45) Date of Patent: May 6, 2025

(54) VIDEO ARCHITECTURE AND FRAMEWORK FOR COLLECTING SURGICAL VIDEO AT SCALE

(71) Applicants: Jack Wade, La Jolla, CA (US); Jason Wade, La Jolla, CA (US)

(72) Inventors: Jack Wade, La Jolla, CA (US); Jason Wade, La Jolla, CA (US)

( * ) Notice: Subject to any disclaimer, the term of this patent is extended or adjusted under 35 U.S.C. 154(b) by 74 days.

(21) Appl. No.: 17/665,438

(22) Filed: Feb. 4, 2022

(65) Prior Publication Data

US 2022/0249195 A1 Aug. 11, 2022

Related U.S. Application Data

(60) Provisional application No. 63/146,530, filed on Feb. 5, 2021.

(51) Int. Cl.
*A61B 90/00* (2016.01)
*G16H 10/60* (2018.01)
*G16H 20/40* (2018.01)
*G16H 30/40* (2018.01)

(52) U.S. Cl.
CPC .......... *A61B 90/361* (2016.02); *G16H 10/60* (2018.01); *G16H 20/40* (2018.01); *G16H 30/40* (2018.01); *A61B 2090/3612* (2016.02)

(58) Field of Classification Search
CPC .......... A61B 90/361; A61B 2090/3612; G16H 20/40; G16H 10/60; G16H 30/40

USPC .......................................................... 348/61
See application file for complete search history.

(56) References Cited

U.S. PATENT DOCUMENTS

| | | | | |
|---|---|---|---|---|
| 2013/0262564 | A1* | 10/2013 | Wall | H04N 21/812 709/203 |
| 2017/0076501 | A1* | 3/2017 | Jagga | G06T 7/73 |
| 2017/0258526 | A1* | 9/2017 | Lang | H05K 999/99 |
| 2018/0338802 | A1* | 11/2018 | Wade | G16H 20/40 |
| 2021/0313052 | A1* | 10/2021 | Makrinich | G06V 10/764 |
| 2021/0382559 | A1* | 12/2021 | Segev | G06V 10/806 |

OTHER PUBLICATIONS

Ashutosh et al., Select menu items from keyboard, Microsoft, Jul. 8, 2011, https://answers.microsoft.com/en-us/msoffice/forum/all/select-menu-items-from-keyboard-like-altletter-in/7a6ee809-d274-4868-a5d0-2b1dfd7d0ba7 (Year: 2011).*

* cited by examiner

*Primary Examiner* — James E Springer
(74) *Attorney, Agent, or Firm* — Olivo IP Law Group, P.C; John W. Olivo, Jr.

(57) ABSTRACT

The present invention is a foundational video architecture and a framework for collecting surgical video at an enterprise scale. It enables hospitals to ingest, manage, and fully utilize patient surgical video within the hospital and to share video with designated users outside of the hospital. It is a passive solution that automatically records video during surgery and provides key clips post surgery. It stores video to the cloud and integrates videos to the patient's Electronic Health Record (EHR).

14 Claims, 12 Drawing Sheets

Symbols (text strings)

| | |
|---|---|
| $MMDDYY | Date |
| $HHSS | Time Stamp |
| $PROCID | Procedure ID |
| $PATID | Patient ID |
| $PRCode | Procedure code |
| $PROCTITLE | Procedure Title |
| $PATNAME | Patient name |
| $DRNAME | Surgeon |

Terminology

Session, procedure
Collaborators, Participants
Preferences, defaults for {procedure, surgeon, procedure}

Databases

| | |
|---|---|
| Procedure | ID, code, title, description, each session |
| SnapShots | ID, SMPTE, Image, Doctor, Date-Time, Annotation |
| Annotations | Doctor source, audio track, graphic events, ... |
| Video | Procedure, equipment setup |
| Narrations | Procedure, Snapshot, Audio |
| Collaborators | Name, specialty, and IP Address |
| Surgeons | Name, specialty, Screen preferences |

Stripe Font Sizes:
12pt: ABCDEFGHIJKLMNOPQRSTUVWXYZ 0123456789
14pt: ABCDEFGHIJKLMNOPQRSTUVWXYZ 0123456789
16pt: ABCDEFGHIJKLMNOPQRSTUVWXYZ 0123456789
18pt: ABCDEFGHIJKLMNOPQRSTUVWXYZ 0123456789
20pt: ABCDEFGHIJKLMNOPQRSTUVWXYZ 0123456789

VIDEO ARCHITECTURE AND FRAMEWORK FOR COLLECTING SURGICAL VIDEO AT SCALE

PRIORITY CLAIMS

This application claims the benefit of U.S. Provisional Application Ser. No. 63/146,530, filed on Feb. 5, 2021, the contents of which are incorporated herein.

BACKGROUND

Surgical video is playing an increasing role in modern medicine. Indeed, most surgeons reported using videos to prepare for surgery and indicated that YouTube was the preferred source. There is growing support for intraoperative video recording. In the past, the widespread adoption of intraoperative video has been hampered by legal concerns relating to healthcare provider liability, and patient privacy.

Video analysis allows studying both surgical technique (i.e. the details of how an operation is conducted) and surgical skill (i.e. how well a surgeon performs a procedure). There is growing enthusiasm to tackle the challenges of directly evaluating and improving surgeon performance using intraoperative video.

Surgical video in combination with intraoperative computer vision opens the door to real-time, automated surgical analysis. It enables artificial intelligence (AI) to analyze and interpret videos during an operation. By teaching the AI to understand what is happening during surgeries, the AI will develop capabilities to assist surgeons in assessing the risk for a postoperative complication or even provide surgeons with additional data to improve operating room decisions.

SUMMARY OF THE INVENTION

To fully realize the potential benefits surgical video requires a secure and highly scalable compute infrastructure that networks various sources of surgical video and supports saving, storing, managing processing and distributing vast volumes of video.

The present invention, referred to herein as Cloudcapture is a foundational video architecture and a framework for collecting surgical video at an enterprise scale. It enables hospitals to ingest, manage, and fully utilize patient surgical video within the hospital and to share video with designated users outside of the hospital. It is a passive solution that automatically records video during surgery and provides key clips post surgery. It stores video to the cloud and integrates videos to the patient's Electronic Health Record (EHR).

These and other aspects, objects, features and advantages of the present invention, are specifically set forth in, or will become apparent from, the following detailed description of an exemplary embodiment of the invention.

BRIEF DESCRIPTION OF THE DRAWINGS

FIG. 10 is an operating environment system view of the structures and databases of the present invention.

DETAILED DESCRIPTION OF THE PREFERRED EMBODIMENT

Figure 1:
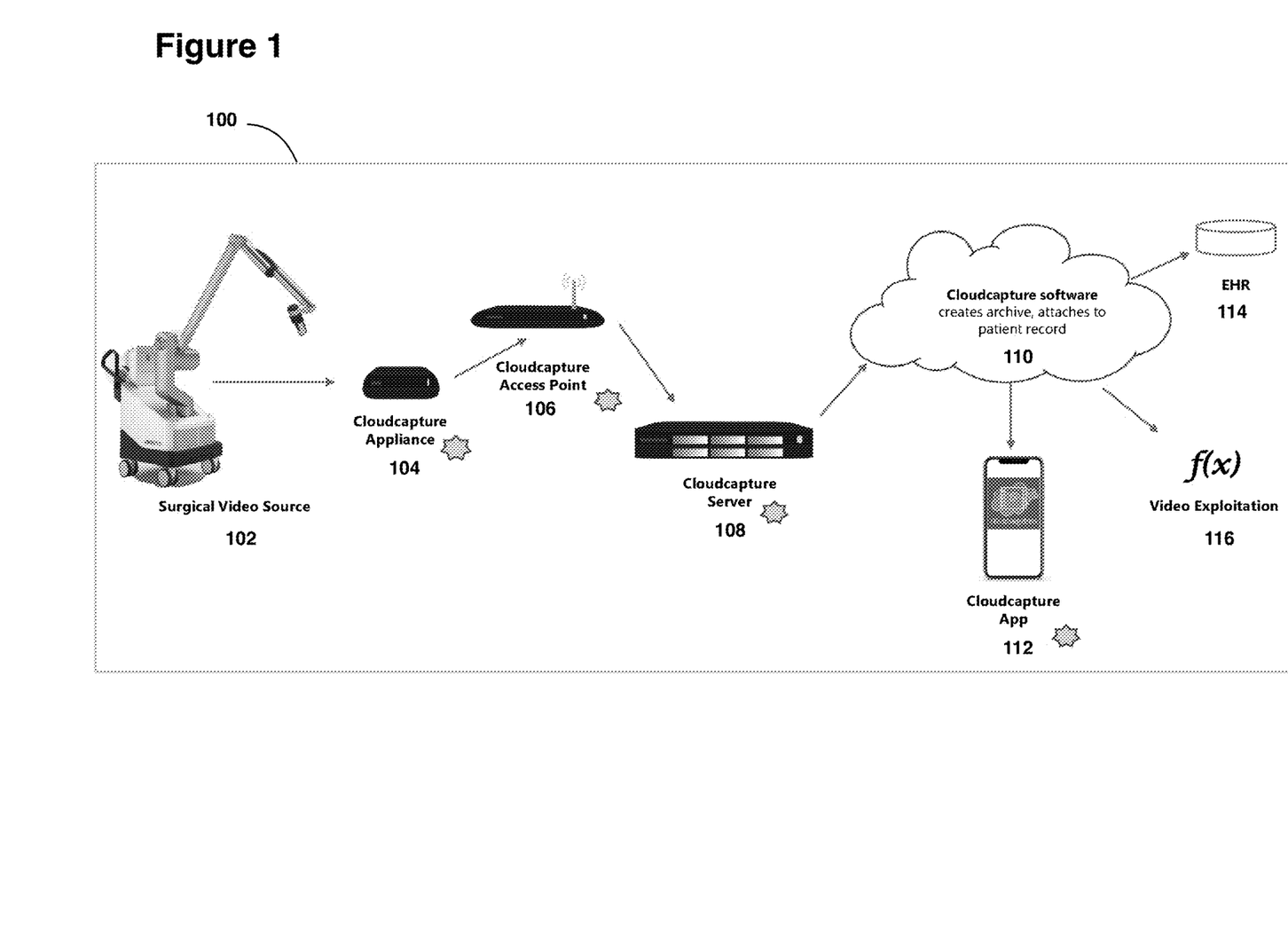
FIG. 1 is a diagram of the operating environment and system view of the present invention.

FIG. 1 is a diagram of the operating environment and system view of the present invention. In accordance with the preferred embodiment of the present invention, the Cloudcapture architecture 100 connects a surgical video source 102 such as a video endoscope to a Cloudcapture appliance 104 within the surgical theater. The Cloudcapture appliance 104 connects to a Cloudcapture Access Point 106, typically using a wireless connection. The Cloudcapture Access Point 106 communicates with a Clouldcapture Server 108, typically using a wireless connection. Multiple appliances can be connected to a network which may include a Cloudcapture server 108 or connect to a cloud service 110 that runs the Cloudcapture server software, which can be implemented via the Cloudcapture mobile application 112, electronic health records (EHR) 114 and video 116.

Figure 2:
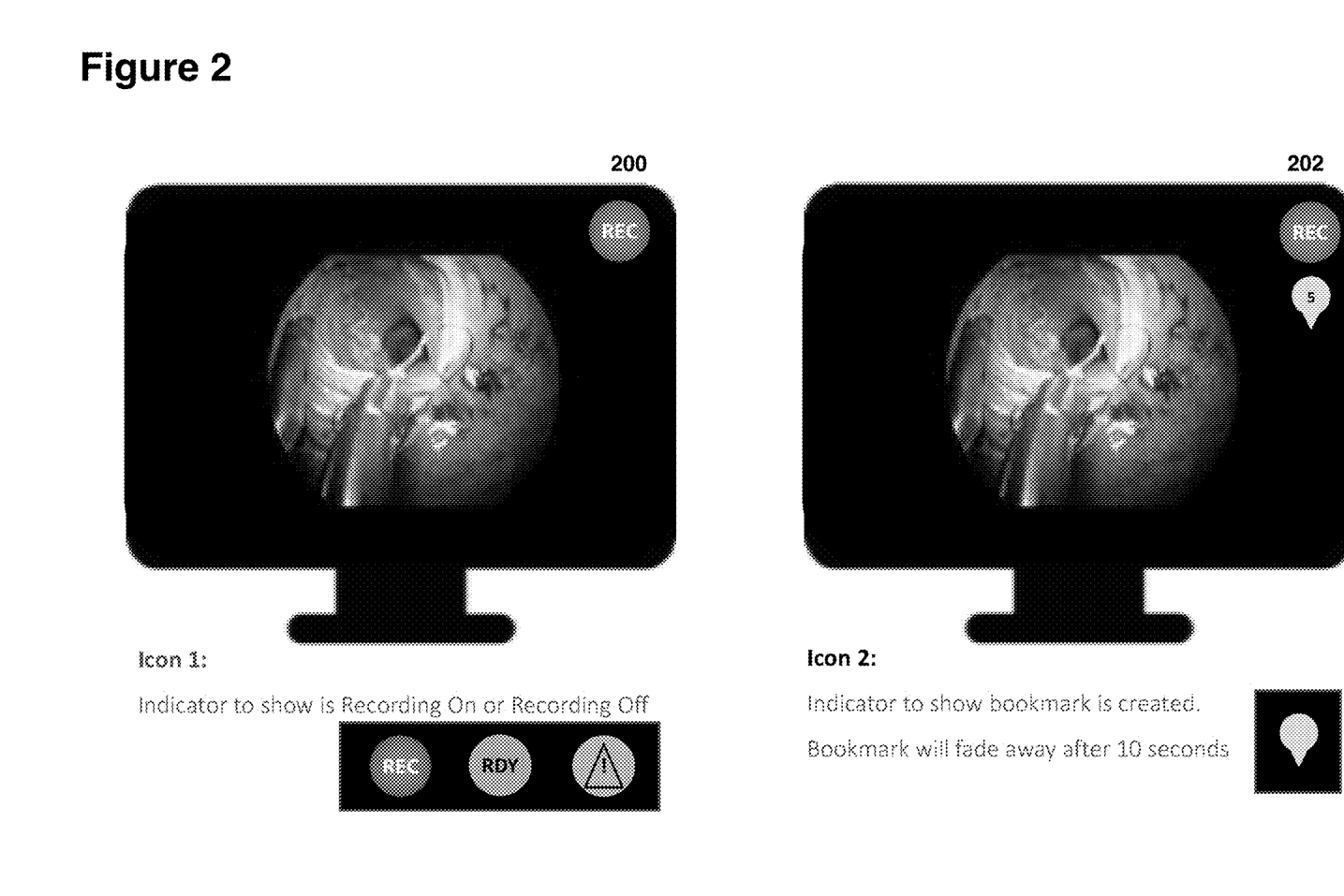
FIG. 2 is an image of the UI that might be display on a surgical display during a medical procedure.

FIG. 2 is an image of the UI that might be display on a surgical display during a medical procedure. In accordance with the preferred embodiment of the present invention, the Cloudcapture appliance provides core capabilities including capturing video and sending it to a Cloudcapture server, recording video locally with the ability to take snapshots 200, i.e. screenshots for future viewing, and a grid tool that overlays a grid so the user can locate, measure and tag 202 anatomical regions during surgery. Additional, capabilities as previously disclosed in the "Surgeon's Desktop" can be added to the appliance to further aid a surgeon during a procedure. These include Timers and Counters, Annotation with Voice Overs and Virtual Pointer, Video Stabilizer, ICG Quantification, Polyp Finder, Tissue Analyzer.

Figure 3:
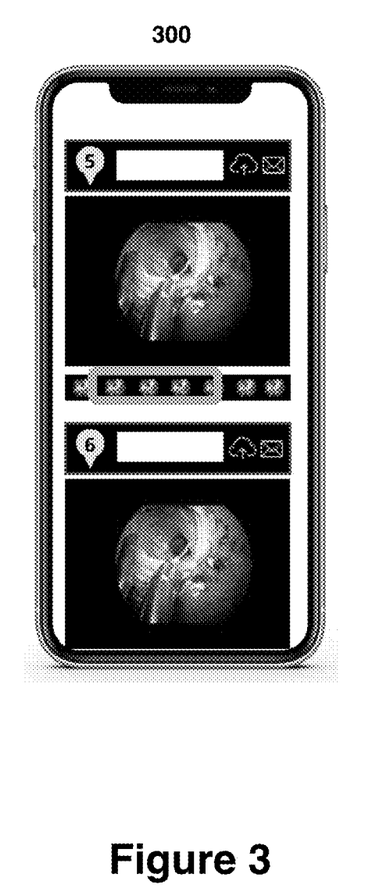
FIG. 3 is an image of a UI that might be displayed on a mobile app to view imagery after a medical procedure.

FIG. 3 is an image of a UI that might be displayed on a mobile app to view imagery after a medical procedure. In a preferred embodiment, the Cloudcapture UI 300 overlayed on the surgical display during medical procedures consists of 1) a top stripe, 2) a bottom stripe, 3) a main menu panel, 4) sub-menu panels, 5) functions that are listed in submenu panels. Users can interact with the UI by issuing commands by voice, click, or keyboard. I detailed description of a preferred embodiment envisions a surgical display size of 3840×2160 pixels.

Figure 4:
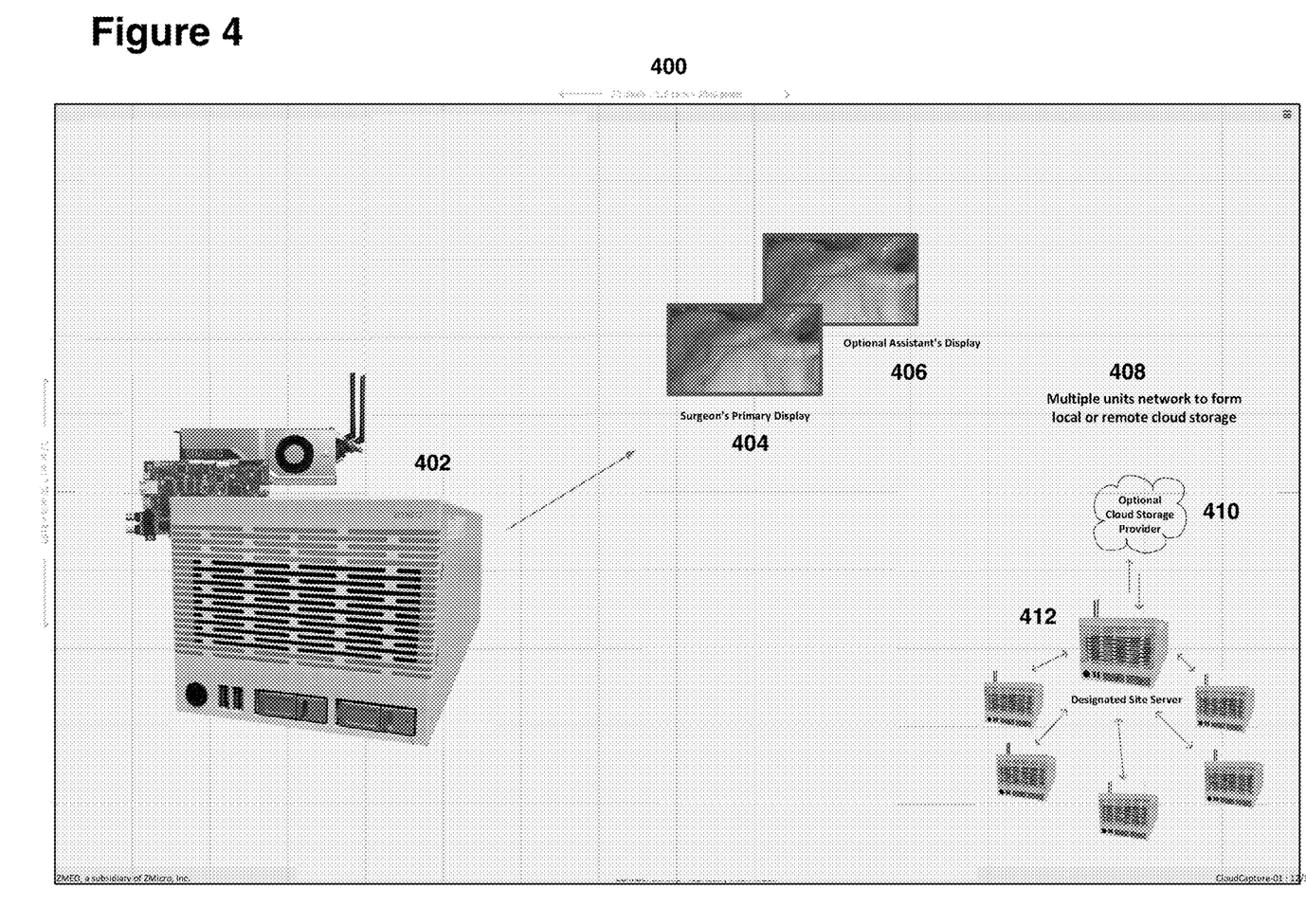
FIG. 4 is an overview of a network of multiple units of the present invention.

FIG. 4 is an overview of a network 400 of multiple units of the present invention. In accordance with the preferred embodiment of the present invention, the Cloudcapture server software 402 creates a video archive, attaches the video 404 and 406 to a patient record, and optionally applies video enhancement or video analysis. Multiple units network to form local or remote cloud storage 408 and an optional cloud storage provider 410 can be used in communication with the designated site server 412. The videos and related metadata saved on the Clouldcapture Server 412 can be retrieved by end-users such as doctors using the Clould-capture mobile application that runs on smartphones.

The process flow for a surgeon in the operating room before a procedure can be described as follows:

1. Open iPhone App to initiate a recording session
2. Enter patient ID
3. Identify hardware in OR: use NFC on iPhone to "tap" each CC device & the CC access point
4. Start recording initiated on iPhone App
5. Surgeon identifies video "bookmarks" during a procedure by voice, foot pedal, or other-tag gets associated with video from CC device
6. Stop recording command
7. CC Server transcodes and provides clips of all bookmarks on App ASAP
8. Surgeon edits and sends clips to email/Playback Health/text/etc.

Figure 5:
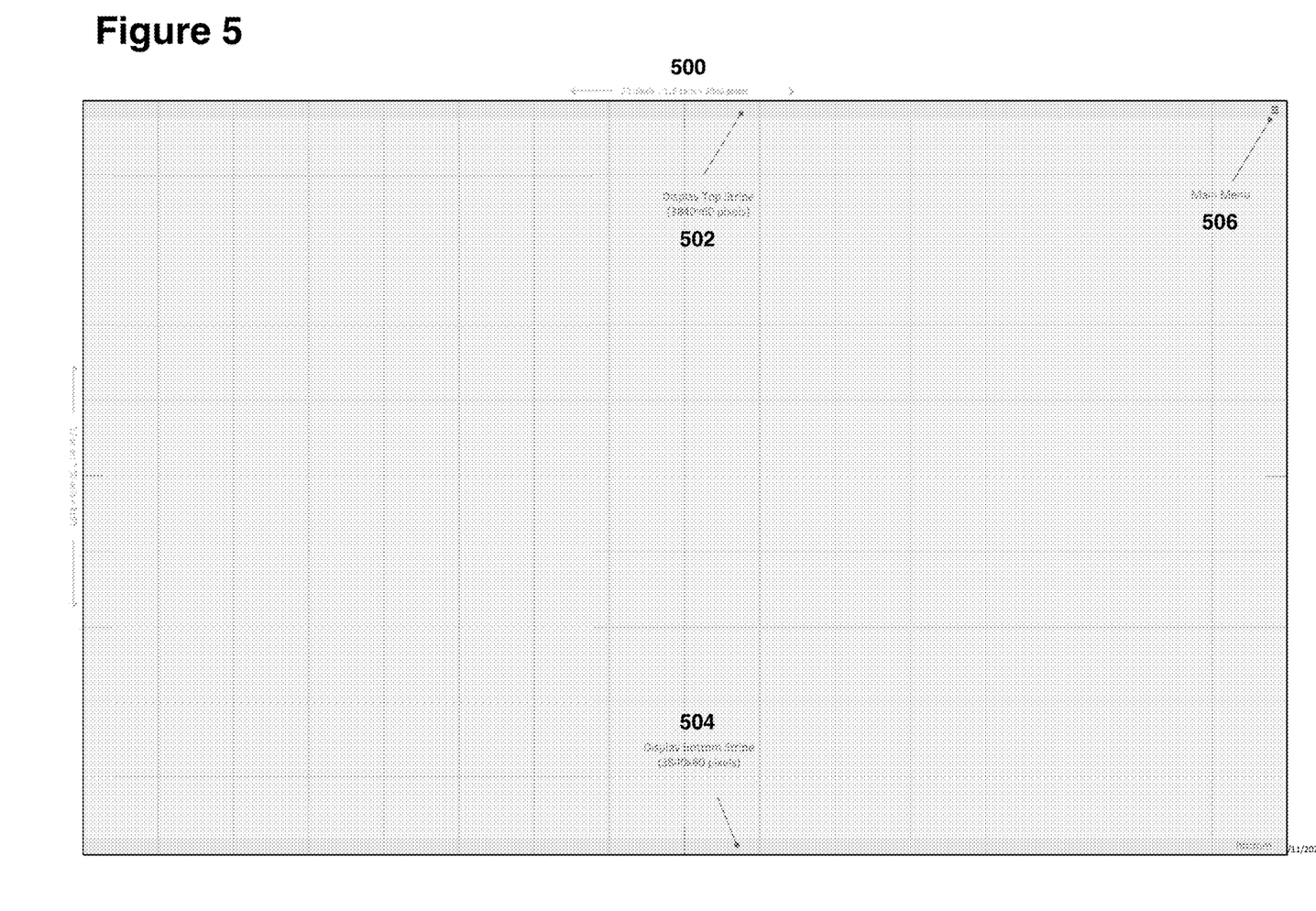
FIG. 5 is an operating environment system view of the UI top and bottom stripes of the present invention.

FIG. 5 is an operating environment system view of the UI top and bottom stripes of the present invention. In accordance with the preferred embodiment of the present invention, the top 502 and bottom 504 information stripes are narrow information stripes that span the entire width of the top 502 and bottom 504 edges of the display window 500 (3840×2160) and also at top and bottom of every video frame snapshot (full width of frame, 240 or as scaled up). The vertical pixel depths are: 60 Pixels for the full display window stripes (3840×60); and 27 Pixels for each video frame snapshot (240×27, 480×27, etc.). The physical desktop display features top 502 and bottom 504 stripes that span the entire width of the display 500 and provide the 3840×60 pixel area for text or graphics. Multiple text lines are possible depending on the font size selected. The systems administrator defines the stripe format by providing a prototype text line using symbolic keyword reference. The display top stripe will always be included in any desktop design. It displays the basic metadata identifying the patient and procedure as selected by the site system administrator. Symbolic keywords reference each metadata term when formatting text. Each site will have a list of its metadata terms. Example metadata symbols are:

$PROCID—Procedure ID
$PATID—Patient ID
$PATNAME—Patient Name
$DRNAME—Lead Surgeon
$MMDDYY—Date-Time Stamp The bottom Display stripe is available to software functions for a variety of purposes. Examples may include:

a) Elapsed timer (default lower right hh:mm)
b) Spoken keywords relevant to the currently active function
c) Waypoint notices from an event structured procedure
d) Incoming message from a collaborator monitoring the procedure
e) Other The main menu panel 506 is always located at the upper right corner of both the Primary and Assistant displays. The menu 506 is illustrated in an open mode with the submenu selections displayed as an ordered list. It may also be collapsed into a small single stripe. The screen pixels allocated for the Menu Panel 506 is 600 across×1890 (20×70 Visio template cells). Each submenu horizontal stripe, when closed, is 600 pixels wide (20×30). When opened, the submenu panel extends downward as needed.

Figure 6:
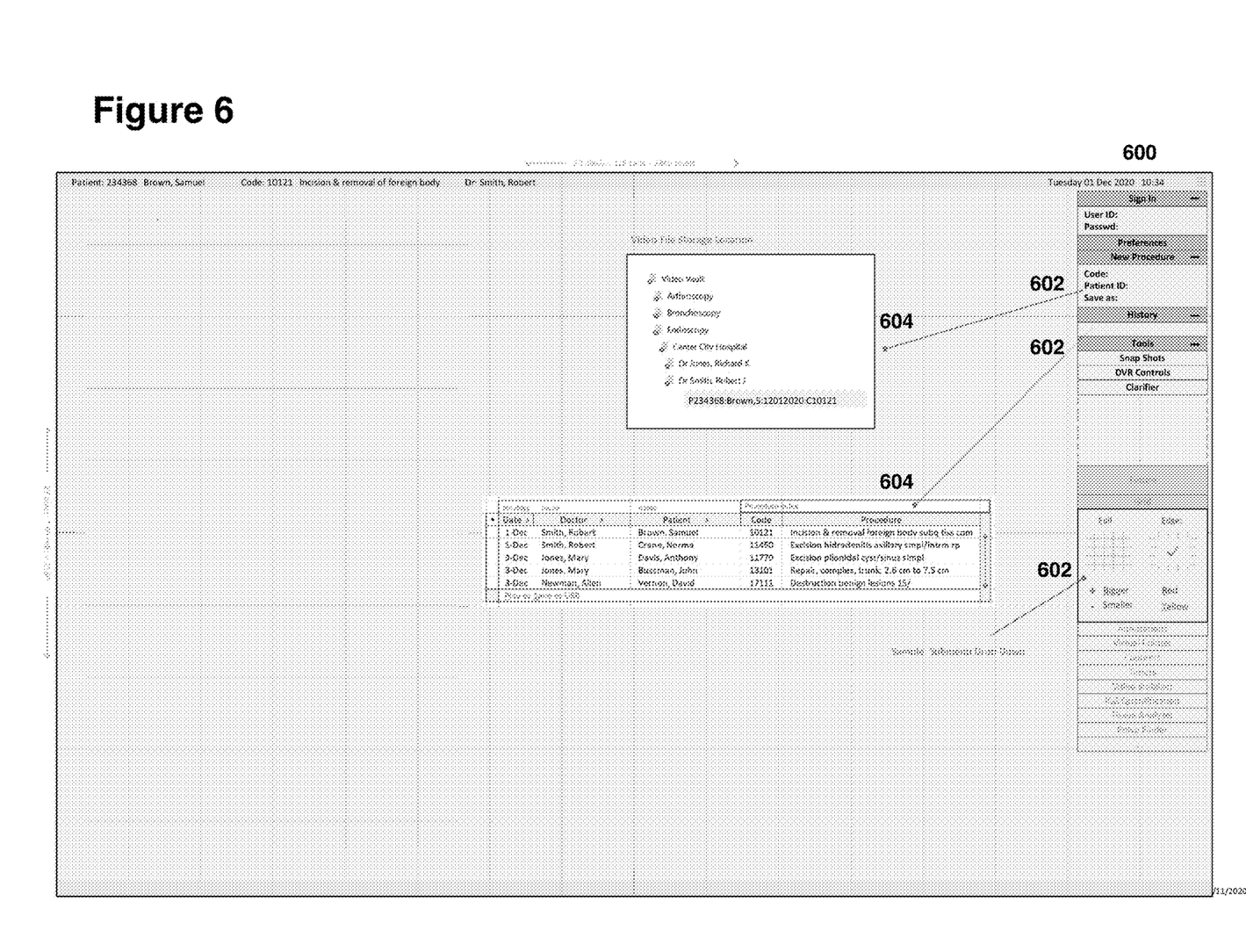
FIG. 6 is an operating environment system view of the menu panels of the present invention.

FIG. 6 is an operating environment system view of the menu panels of the present invention. In accordance with the preferred embodiment of the present invention, When the main menu panel 600 is open, it provides an entry for each function as a submenu 602. Each function is represented by a "title stripe" that clicks open into a scratchpad work panel 604 to execute its operations.

The preferences submenu 602 consists of defaults selected for the current surgeon or procedure. Once the preferences are selected, the submenu 602 can be closed until a new procedure or a change is needed. Selections are saved and recalled when the Surgeon/Procedure is used again. For example, the Grid Tool. The Pop ups submenu consists of functions that remain active until no longer needed. For example, the Annotation Tools. The built-in submenu consists of functions that were selected to be part of the default screen layout configured for a specific surgeon or procedure. These functions have a dedicated display area. For example, the SnapShots, Main video window, DVR tools.

Submenu functions that are not part of the default screen layout still need a dedicated display area ("scratchpad") 604 to execute their tasks. Two types of "scratchpad" display panels 604 are available. The Drop Down can be expanded in place within the main menu panel using same width and as much depth as needed, subject to availability. The Grid tool is shown opened as a Drop Down. The Pop Up can be used for functions that require a large scratchpad area can pop up an arbitrary size scratchpad window anchored to a specified X,Y location, possibly beside or on top of the main video or other windows, for example, the Video Enhancement window. Words in highlighted color are commands and appear in the bottom stripe when the menu selection is active. Commands can be activated by voice, by mouse click, or keyboard of underlined character.

Figure 7:
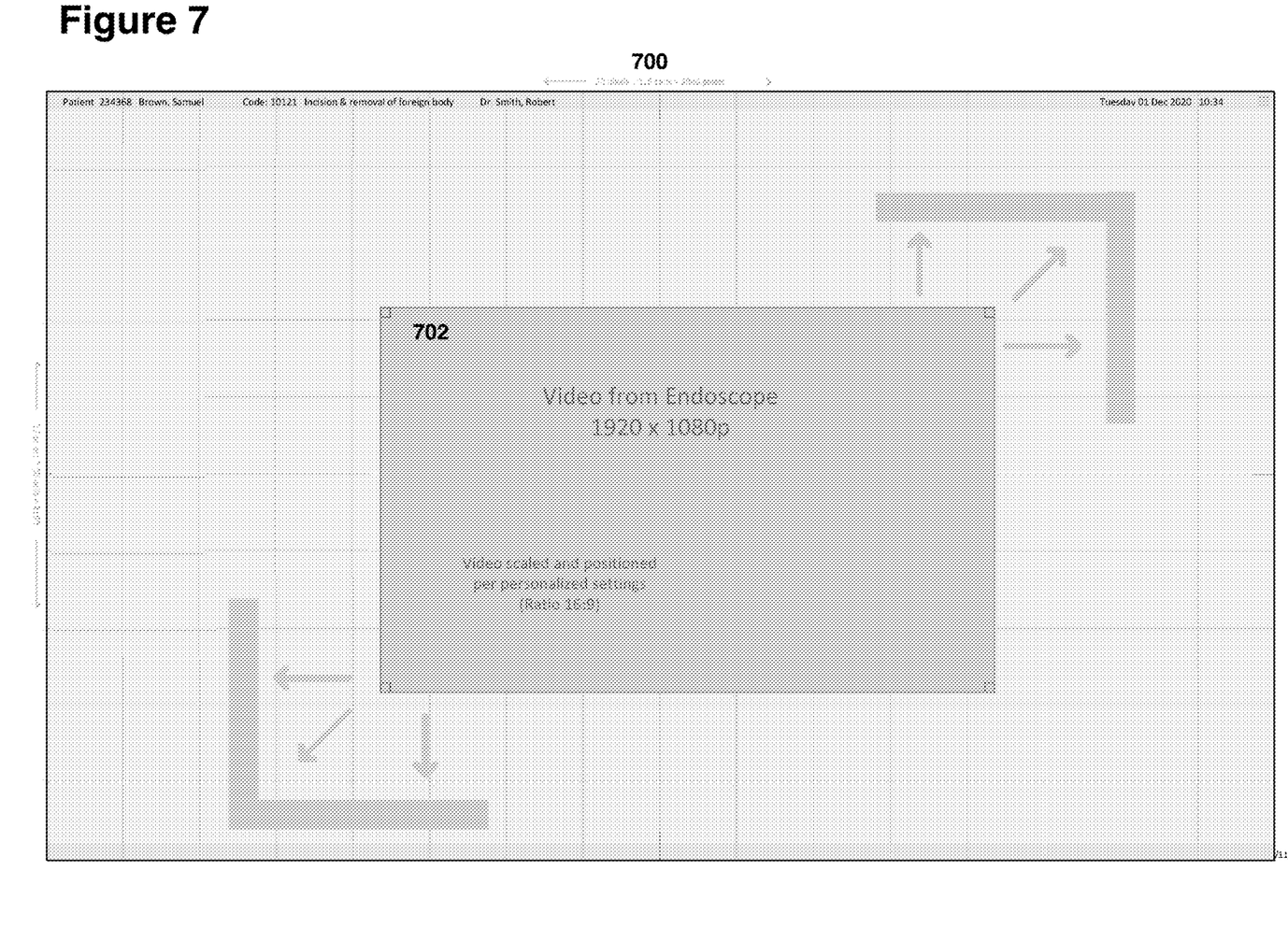
FIG. 7 is an operating environment system view of the main video window of the present invention.

FIG. 7 is an operating environment system view of the main video window of the present invention. In accordance with the preferred embodiment of the present invention, the main video window 700 is comprised of a video stream 702 coming in from the endoscope can be 2K or 4K resolution (1920×1080 or 3840×2160). The initial implementations will most likely be 2K (1920×1080). The layouts illustrated in this initial document assume a 1920×1080 feed that will be scaled up as preferences dictate. When 4K endoscopes become available, 8K monitors might also be available so desktop designs will be created that maximize the desktop based upon the video format and the screen space available. For the present, the site administrators will design desktop configurations for 2K video and 4K monitors to offer options for surgeons to select their preferred setup.

Figure 8:
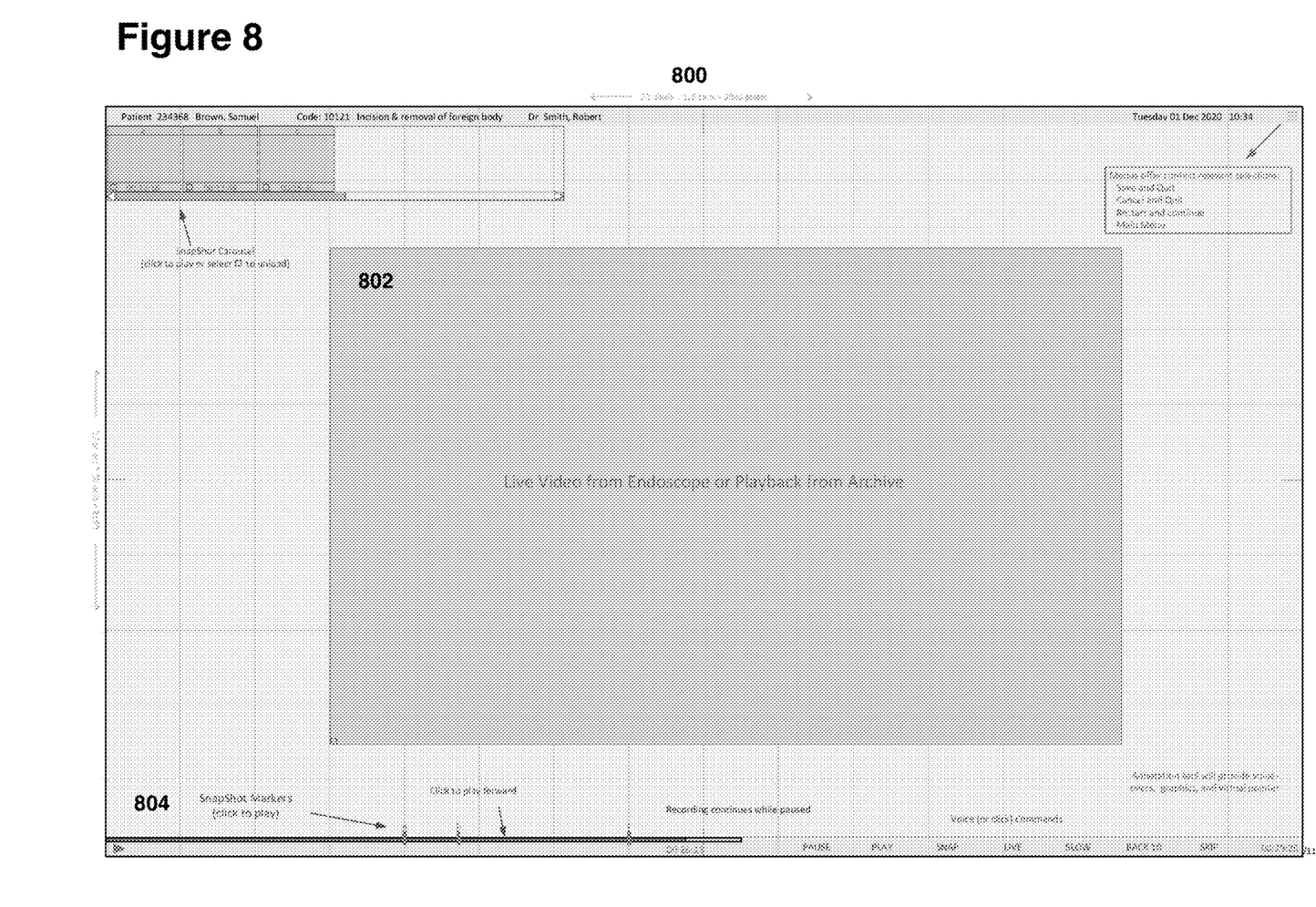
FIG. 8 is an operating environment system view of the DVR tool of the present invention.

FIG. 8 is an operating environment system view of the DVR tool of the present invention. In a preferred embodiment, a DVR Tool 800 enables a user to record and playback surgical video 802 during a medical procedure. On-screen control 804 allows the user to select a portion of the recorded surgical video and to play or pause it when viewing.

Figure 9:
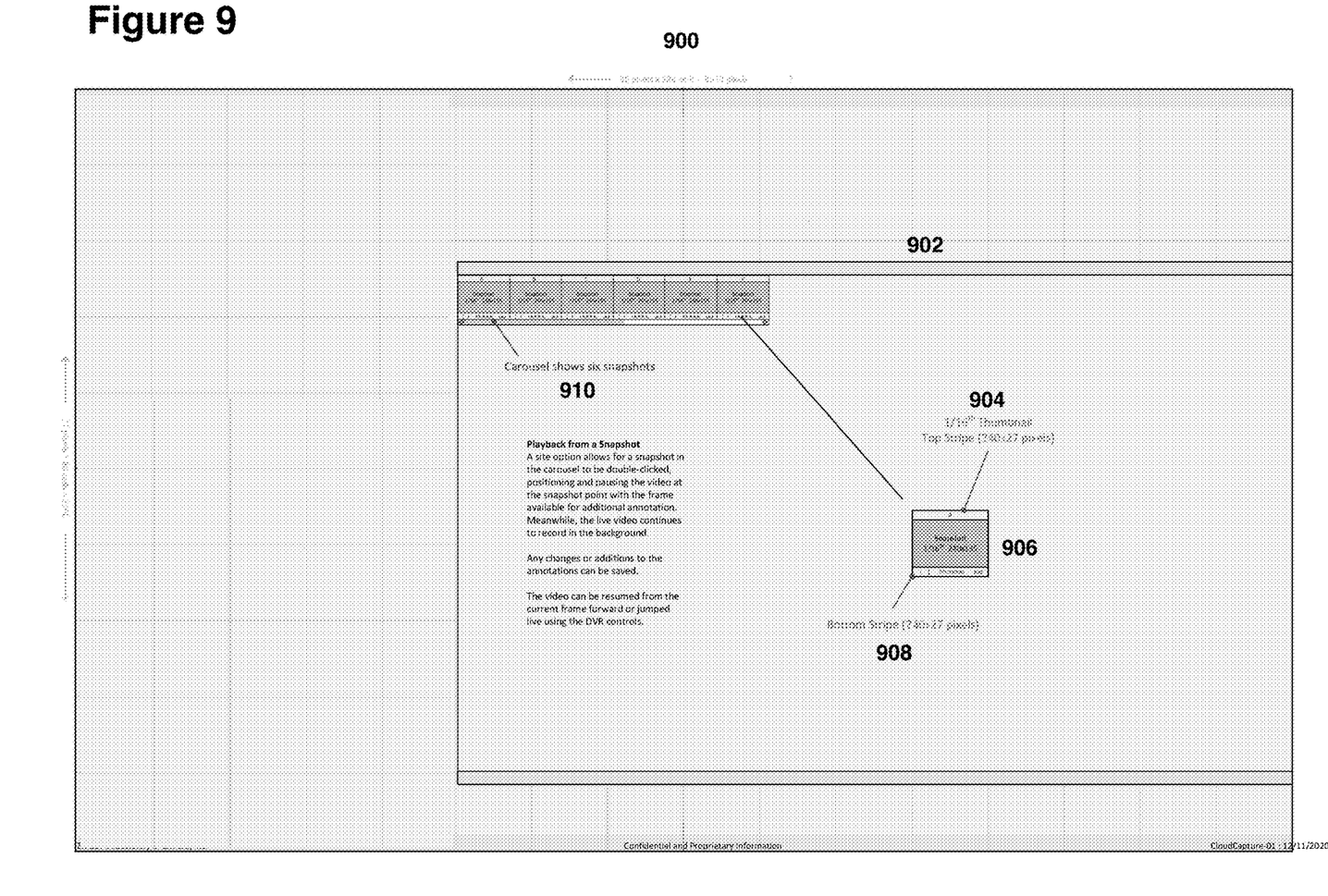
FIG. 9 is an operating environment system view of the snap shots of the present invention.

FIG. 9 is an operating environment system view of the snap shots 900 of the present invention. In accordance with the preferred embodiment of the present invention, a snapshot is a "frame grab" of the current frame from the video being displayed in the main video window 902. Typically, it is a single frame but It can also be used as a bookmark to the starting video frame in a sequence of one or more video frames in a clip. In this case, a second bookmark marks the end point of the clip. Each snapshot creates an entry in the "Snapshot" database maintained for each procedure. The database entry includes a ¹⁄₁₆th scaled image as a thumbnail along with the metadata associated with the frame. Snapshots 900 are a tool designed primarily for the lead surgeon, or the assistant, but in a collaborative mode, any participant can be enabled to collect their own sequence of snapshots (see the discussion on Collaboration). The surgeon commands a snapshot using a verbal command ("SNAP", or "SNAPSHOT"). The assistant may also issue the verbal command, or with a mouse click on the frame snap icon. The database entry includes the information needed to display the snapshot with its reference information.

A Snapshot frame 902 is displayed with 3 components: the top stripe 904 (240×27 pixels); the scaled image 906 (240×135 pixels); and the bottom stripe 908 (240×27 pixels). The top stripe 902 uses an Alpha Identifier (A,B,C,D, . . . ) and can be selected (clicked) to expose a popup metadata panel. The bottom stripe 908 consists of a selection check box, time stamp hh:mm:ss , and audio overlay icon.

The snapshot display carousel 910 is a dedicated display area for six snapshots with a horizontal scroll capability with the following functions: six snapshots scrolling backwards/forwards; clicking the stripe jumps back/forward one frame; and default screen position is 0,0 but can be repositioned. Database entry for each snapshot includes: the procedure ID; the originator (surgeon, or assistant, or a permissioned collaborator); the SMPTE timestamp; the bit flags (selected, . . . , . . . , . . . , . . . ); the snapshot sequential identifier (a, b, c, . . . ); the top stripe; the compressed thumbnail; the bottom stripe; alink to first audio overlay database; a link to first annotation overlay database; and a link to first drag-n-drop to collaborator database. The post procedure options include options to record selected frames to USB or IP Port or to record selected frames to a USB or an IP Port.

FIG. 10 is an operating environment system view 1000 of the structures and databases of the present invention. In accordance with the preferred embodiment of the present invention, the reference diagram show examples of the software structures and databases needed to provide meta data for imagery and generate content for the UI for the surgical displays in a preferred embodiment.

Figure 11:
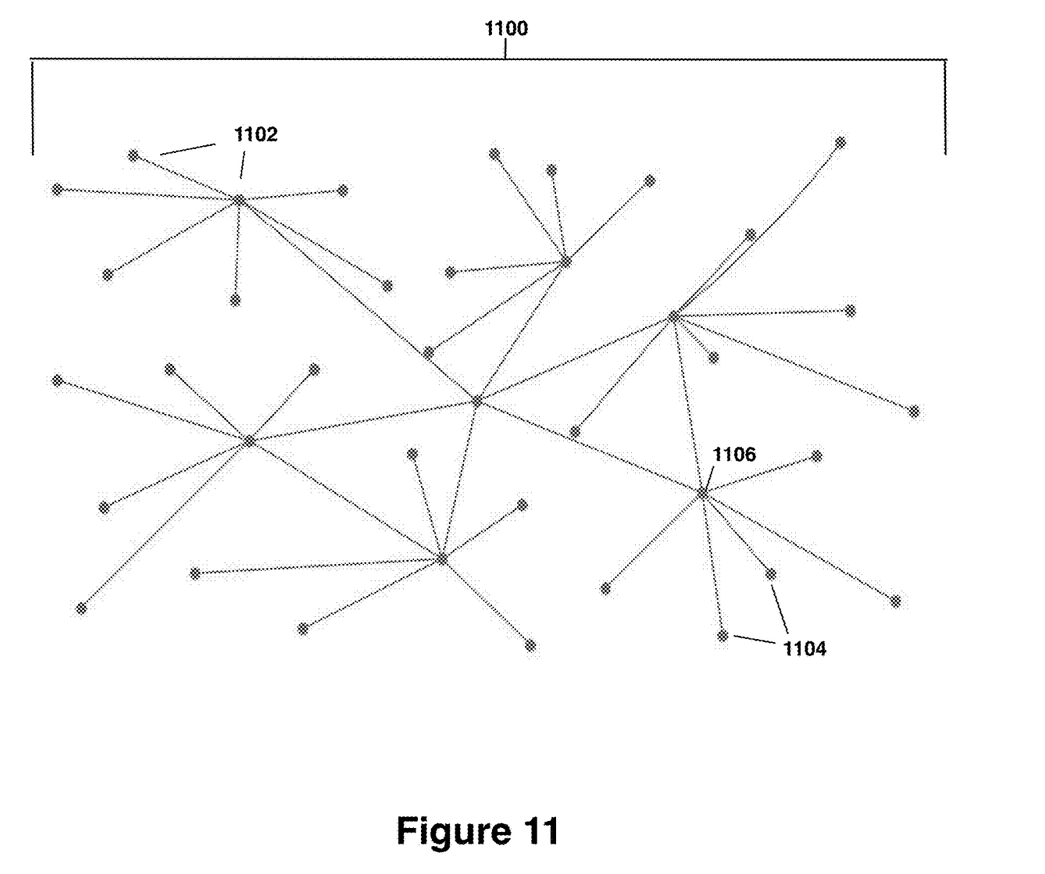
FIG. 11 is a line diagram illustrating a decentralized network.

FIG. 11 is a line diagram illustrating a decentralized network. In accordance with the preferred embodiment of the present invention, the specific architecture of the network can be either decentralized or distributed. FIG. 11, generally represented by the numeral 1100, provides an illustrative diagram of the decentralized network. FIG. 11 depicts each node with a dot 1102. Under this system, each node is connected to at least one other node 1104. Only some nodes are connected to more than one node 1106. According to FIG. 1 (a diagram of the operating environment and system view of the present invention), the network environment of FIG. 11 may be utilized for communication interconnection of all the component parts. In accordance with the preferred embodiment of the present invention, the Cloudcapture architecture connects a surgical video source such as a video endoscope to a Cloudcapture appliance within the surgical theater. The Cloudcapture appliance connects to a Cloudcapture Access Point, typically using a wireless connection. Cloudcapture Access Point communicates with a Clouldcapture Server, typically using a wireless connection. Multiple appliances can be connected to a network which may include a Cloudcapture server or connect to a cloud service that runs the Cloudcapture server software.

Figure 12:
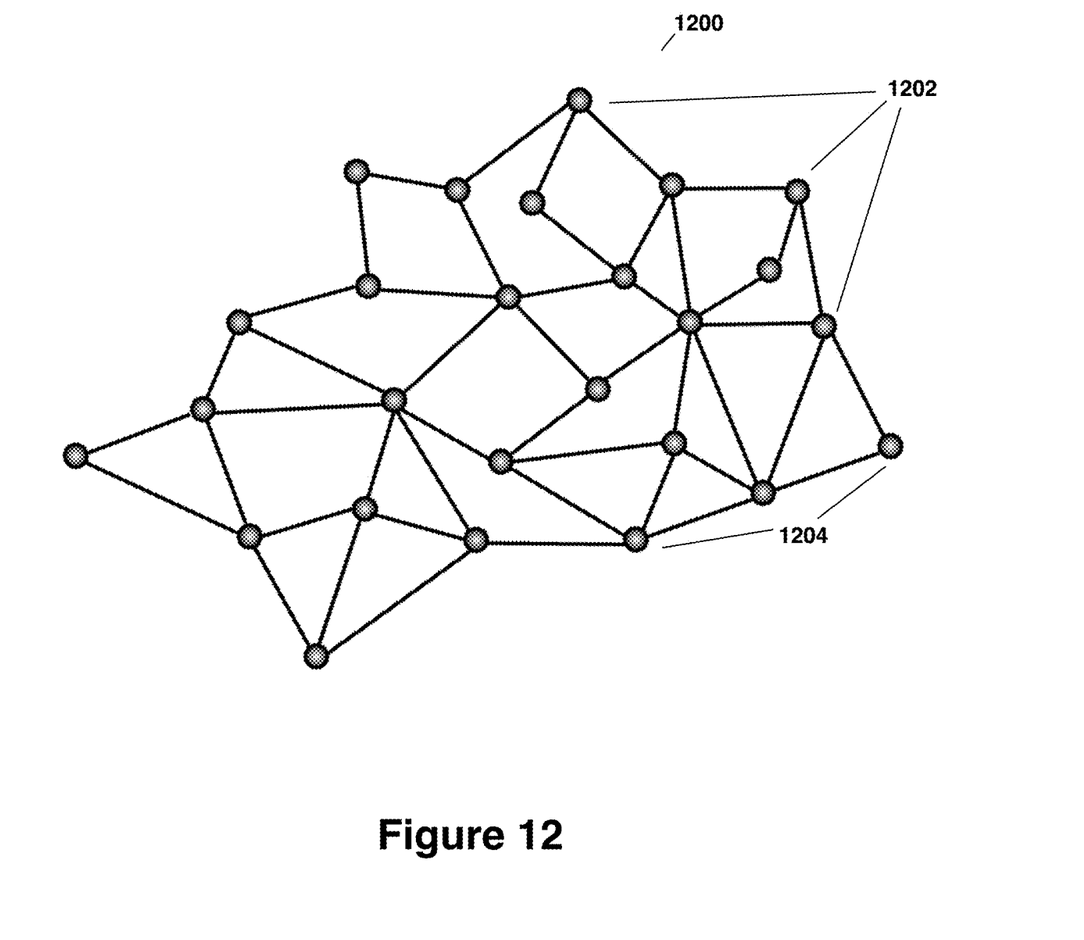
FIG. 12 is a line diagram illustrating a distributed network.

FIG. 12 is a line diagram illustrating a distributed network. For comparison purposes, FIG. 12, which is generally represented by the numeral 1200, illustrates a distributed network. Specifically, the illustration shows the interconnection of each node 1202 in a distributed decentralized network 1200. In accordance with the preferred embodiment of the present invention, each node 801 in the distributed network 1200 is directly connected to at least two other nodes 1204. This allows each node 1202 to transact with at least one other node 1202 in the network. The present invention can be deployed on a centralized, decentralized, or distributed network. Likewise, the system according to FIG. 1 of the present invention and its components may be interconnected by way of the distributed network of FIG. 12.

In one embodiment, each transaction (or a block of transactions) is incorporated, confirmed, verified, included, or otherwise validated into the blockchain via a consensus protocol. Consensus is a dynamic method of reaching agreement regarding any transaction that occurs in a decentralized system. In one embodiment, a distributed hierarchical registry is provided for device discovery and communication. The distributed hierarchical registry comprises a plurality of registry groups at a first level of the hierarchical registry, each registry group comprising a plurality of registry servers. The plurality of registry servers in a registry group provide services comprising receiving client update information from client devices, and responding to client lookup requests from client devices. The plurality of registry servers in each of the plurality of registry groups provide the services using, at least in part, a quorum consensus protocol.

As another example, a method is provided for device discovery and communication using a distributed hierarchical registry. The method comprises Broadcasting a request to identify a registry server, receiving a response from a registry server, and sending client update information to the registry server. The registry server is part of a registry group of the distributed hierarchical registry, and the registry group comprises a plurality of registry servers. The registry server updates other registry servers of the registry group with the client update information using, at least in part, a quorum consensus protocol.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

What is claimed is:

1. A medical software tools system, comprising:
   a tool for sensing surgeon hand movements in connection with surgical camera usage to invoke a video overlay displaying a synthetic visual path starting from an end of a selected instrument onward through an intended path of movement in a specified distance and direction corresponding to an orientation of said tool;
   a grid layout to guide said surgeon hand movements along said synthetic visual path as to determine a placement of various surgical tools by way of said video overlay, and wherein said video overlay enables locating, measuring and tagging anatomical regions during surgery;
   a computer system receiving an image stream from said surgical camera;
   said computer system providing a user interface overlay is adapted for presentation over a surgical image stream and analyzing said surgical image stream and calculating an anticipated direction of movement corresponding to said direction said surgical tool is oriented;
   use of a combination of audio keywords and movements to enable predictive surgical tool movements to assist said surgeon;
   a scratchpad area can pop up and be voice activated so that surgeons may be guided during surgical procedures and wherein said voice activated commentary can appear as text in a submenu while a menu selection is active; and
   a cloud network collects surgical images on an enterprise scale to enable hospitals to ingest, manage, and fully utilize patient surgical video within a hospital network and to share said video with designated users and to automatically record video during said surgery and provide key clips for evaluation of hospital resources and to store said video for integration with patient electronic health records, and wherein said key clips are presented by way of a snapshot carousel that can provide snapshot playbacks.

2. A system according to claim 1 wherein said surgeon may take snapshots of patient surgical conditions to be shared with medical system users.

3. A system according to claim 1 wherein a said cloud network includes a server for creating a video archive and related metadata saved on said server wherein said video archive is accessed by said surgeons using said system and wherein said video archive is automatically attached and updated to a patient's record, and optionally applies video enhancement or video analysis.

4. A system according to claim 1 wherein said cloud network interfaces with smartphones on a mobile application.

5. A system according to claim 4 wherein video images may be captured by said smartphones and entered into said system for storage in a video archive on said mobile application.

6. A method of using medical software tools for performing surgical procedures, comprising:
   using a tool for sensing surgeon hand movements in connection with surgical camera usage to invoke a video overlay displaying a synthetic visual path starting from an end of a selected instrument onward through an intended path of movement in a specified distance and direction corresponding to an orientation of said tool;
   using a grid layout to guide said surgeons along said synthetic visual path as to determine a placement of various surgical tools by way of said video overlay;
   locating, measuring and tagging anatomical regions during surgery;
   enabling a computer system for receiving an image stream from said surgical camera;
   said computer system providing a user interface overlay adapted for presentation over a surgical image stream and analyzing said surgical image stream and calculating an anticipated direction of movement corresponding to said direction said surgical tool is oriented;
   using of a combination of audio keywords and movements to enable predictive movements of said surgical tool to assist said surgeon;
   displaying a scratchpad area with voice activated commands so that surgeons may be guided during said surgical procedures;
   generating voice activated commentary and transcribing it as text in a submenu while a menu selection is active; and
   using a cloud network to collect surgical images on an enterprise scale to enable hospitals to ingest, manage, and fully utilize patient surgical video within a hospital network and to share said video with designated users and to automatically record video during surgery and provide key clips for evaluation of hospital resources and to store said video for integration with patient electronic health records presenting said snapshots by way of a snapshot carousel that can provide a playback of said snapshot.

7. A method according to claim 6 wherein said surgeon may take snapshots of patient surgical conditions to be shared with medical system users on said snapshot carousel with customized settings for said snapshot playback.

8. A method according to claim 6 wherein said cloud network includes a server for creating a video archive and related metadata saved on said server wherein said video archive may be accessed by said surgeon using said system and wherein said video archive is automatically attached and updated to a patient's record, and optionally applies video enhancement or video analysis.

9. A method according to claim 6 wherein said cloud network interfaces with smartphones on a mobile application.

10. A method according to claim 9 wherein video images may be captured by said smartphones and entered into said system for storage in a video archive on said mobile application.

11. A medical software tools system, comprising:
a tool for sensing surgeon hand movements in connection with surgical camera usage to invoke a video overlay displaying a synthetic visual path starting from an end of a selected instrument onward through an intended path of movement in a specified distance and direction corresponding to an orientation of said tool;
a grid layout to guide said surgeon hand movements along said synthetic visual path as to determine a placement of various surgical tools by way of said video overlay;
a display for a scratchpad area with voice activated commands so that surgeons may be guided during surgical procedures;
a computer system receiving an image stream from said surgical camera;
said computer system providing a user interface overlay adapted for presentation over a surgical image stream and analyzing said surgical image stream and calculating an anticipated direction of movement corresponding to said direction said surgical tool is oriented;
use of a combination of keywords and movements to enable predictive surgical tool movements to assist said surgeon; and
a cloud network collects surgical images on an enterprise scale to enable hospitals to ingest, manage, and fully utilize patient surgical video within a hospital network and to share said video with designated users and to automatically record video during surgery and provide key clips for evaluation of hospital resources and to store said video for integration with patient electronic health records, wherein said surgeon captures snapshots of patient surgical conditions to be shared with medical system users and wherein said cloud network includes a server for creating a video archive and related metadata saved on said server wherein said video archive may be accessed by said surgeon using said system and a snapshot carousel wherein a user may select said snapshots presented in said snapshot carousel and generate a snapshot playback.

12. A system according to claim 11 wherein said cloud network interfaces with smartphones through a mobile application.

13. A system according to claim 12 wherein video images may be captured by said smartphones and entered into said system for storage in said video archive on said mobile application.

14. A system according to claim 11 wherein a keyboard may be used to activate commands by highlighting them as text in a submenu while a menu selection is active.

* * * * *